(12) United States Patent
Hanner (10) Patent No.: US 6,419,691 B1
(45) Date of Patent: Jul. 16, 2002

(54) THERMAL ENERGY THERAPY

(76) Inventor: Milene H. Hanner, 563 Quaker Ridge Ct., Arnold, MD (US) 21012

( * ) Notice: Subject to any disclaimer, the term of this patent is extended or adjusted under 35 U.S.C. 154(b) by 0 days.

(21) Appl. No.: 09/533,589

(22) Filed: Mar. 23, 2000

(51) Int. Cl.[7] .................................................. A61F 7/00
(52) U.S. Cl. ........................ 607/108; 607/114; 607/112
(58) Field of Search ................................ 607/112, 114, 607/108; 602/2, 14

(56) References Cited

U.S. PATENT DOCUMENTS

| | | | | |
|---|---|---|---|---|
| 3,463,161 A | * | 8/1969 | Andrassy | 607/110 |
| 3,900,035 A | * | 8/1975 | Welch et al. | 607/108 |
| 4,462,224 A | * | 7/1984 | Dunshee et al. | 62/530 |
| H759 H | * | 4/1990 | Jones | 607/114 |
| 5,172,689 A | * | 12/1992 | Wright | 607/104 |
| 5,176,134 A | * | 1/1993 | Hudson | 607/114 |
| 5,304,216 A | * | 4/1994 | Wallace | 607/112 |
| 5,507,792 A | * | 4/1996 | Mason et al. | 607/104 |
| 5,662,695 A | * | 9/1997 | Mason et al. | 607/96 |
| 5,785,716 A | * | 7/1998 | Bayron et al. | 607/108 |
| 6,017,606 A | * | 1/2000 | Sage et al. | 428/68 |
| 6,033,432 A | * | 3/2000 | Augustine et al. | 607/96 |
| 6,238,427 B1 | * | 5/2001 | Matta | 607/104 |

* cited by examiner

Primary Examiner—Roy D. Gibson
Assistant Examiner—Jocelyn Ram
(74) Attorney, Agent, or Firm—William L. Klima; Law Offices of William L.Klima, PC (57) ABSTRACT

A device for applying therapeutic thermal energy to a human or animal includes a deformable and resilient first layer sealingly connected to a deformable and resilient second layer along a common perimeter, the first layer further sealingly connected to the second layer along a plurality of curvilinear paths within the perimeter, the paths defining a plurality of channels between the first layer and the second layer, the paths being configured to allow articulation between adjacent channels, each channel having at least one end defined by the common perimeter, the at least one end of each channel being directly adjacent at least one end of another channel and, each channel being at least partially filled with a medium.

16 Claims, 6 Drawing Sheets

THERMAL ENERGY THERAPY

FIELD OF THE INVENTION

The present invention is related to the therapeutic application of thermal energy, specifically, heat or cold, to a human or animal. More specifically, the present invention is related to devices and methods of manufacturing devices for applying thermal energy to a human or animal.

BACKGROUND OF THE INVENTION

There are many devices available for conducting thermal therapy. Some of these devices are extremely simple, for example, many households maintain an ice pack characterized by a gel filled bag in the freezer. Some of these devices are extremely complex, for example, some devices circulate a temperature controlled medium throughout a jacket or housing which enshrouds an anatomical treatment site.

Providing a device which effectively applies thermal energy to the body of a human has become particularly challenging due to the ever increasing demand to control costs in the health services industry. Health service institutions are now, more than ever before, being forced to purchase devices which are cheaper and unfortunately, less effective. There is thus an urgent need for devices and methods of manufacturing devices for applying thermal energy to a human or animal which provide increased effectiveness without increased cost.

SUMMARY OF THE INVENTION

A first object of the present invention is to provide a device and method of manufacturing a device for applying thermal energy to a human or animal.

A second object of the present invention is to provide an improved device and an improved method of manufacturing a device for applying thermal energy to a human or animal.

A third object of the present invention is to provide a device which applies thermal energy to an anatomical site precisely, for example, to prevent unnecessary application of such energy to portions of the body which do not require such treatment.

A fourth object of the present invention is to provide a device for applying thermal energy which is comfortable for the wearer.

A fifth object of the present invention is to provide a device for applying thermal energy which is easily worn under clothing.

A sixth object of the present invention is to provide a device for applying thermal energy which maintains a uniform dispersion of medium throughout the device.

A seventh object of the present invention is to provide a device for applying thermal energy which is easily secured to the anatomical site where thermal energy would be therapeutic, for example, a device which is provided with straps which may be connected or adjusted with one hand.

An eighth object of the present invention is to provide a device for applying thermal energy which is configured to apply thermal energy to a specific anatomical site, for example, the shoulder, knee, ankle, or breast.

A ninth object of the present invention is to provide a device for applying thermal energy which is beneficial to manufacture, for example, simple in design, easy to assemble, and cost effective.

A tenth object of the present invention is to provide a device for applying thermal energy to a human or animal including a deformable and resilient first layer sealingly connected to a deformable and resilient second layer along a common perimeter, the first layer further sealingly connected to the second layer along a plurality of curvilinear paths within the perimeter, the paths defining a plurality of channels between the first layer and the second layer, the paths being configured to allow articulation between adjacent channels, each channel having at least one end defined by the common perimeter, the at least one end of each channel being directly adjacent at least one end of another channel and, each channel being at least partially filled with a medium.

An eleventh object of the present invention is to provide a method of manufacturing a device for applying thermal energy to a human or animal including the steps of sealingly connecting a deformable and resilient first layer to a deformable and resilient second layer along a common perimeter, maintaining a pre-selected section of the common perimeter open such that the first and second layers remain independent along the pre-selected section of the common perimeter, sealingly connecting the first layer to the second layer along a plurality of curvilinear paths within the perimeter to form a plurality of channels within the perimeter having at least one open end along the pre-selected section of the common perimeter, holding the first and second layers such that the open pre-selected section of the common perimeter is oriented substantially vertically, filling each channel with a medium, and, sealingly connecting the first layer to the second layer along the open pre-selected section of the common perimeter.

The present invention provides a device for applying therapeutic thermal energy to the body of a human or animal. In a preferred embodiment, the present invention provides a device which includes a first layer and a second layer which are sealingly connected along a common perimeter and along a plurality of curvilinear paths within the perimeter, the paths defining a plurality of channels between the first layer and the second layer, the paths being configured to allow articulation between adjacent channels, each channel having at least one end defined by the common perimeter, the at least one end of each channel being directly adjacent at least one end of another channel and, each channel being at least partially filled with a medium.

The present invention further provides a method of manufacturing a device for applying thermal energy to a human or animal including the steps of sealingly connecting a deformable and resilient first layer to a deformable and resilient second layer along a common perimeter, maintaining a pre-selected section of the common perimeter open such that the first and second layers remain independent along the pre-selected section of the common perimeter, sealingly connecting the first layer to the second layer along a plurality of curvilinear paths within the perimeter to form a plurality of channels within the perimeter having at least one open end along the pre-selected section of the common perimeter, holding the first and second layers such that the open pre-selected section of the common perimeter is oriented substantially vertically, filling each channel with a medium, and, sealingly connecting the first layer to the second layer along the open pre-selected section of the common perimeter.

The present invention essentially provides a device which is extremely inexpensive to manufacture and at the same time provides many benefits over conventional means for applying thermal energy to the body. For example, devices according to the present invention provide a uniform application of medium over the treatment site, are easily secured to the body with optional straps, and may easily be worn under clothing. Moreover, devices according to the present invention easily adapt to the surface contours of the treatment site and some preferred embodiments of the device are directed specifically to the application of thermal energy, either hot or cold, to the shoulder, knee, ankle and breast. In sum, the present invention provides an improvement to the art of therapeutic thermal energy application.

DETAILED DESCRIPTION OF THE PREFERRED EMBODIMENTS

Figure 1:
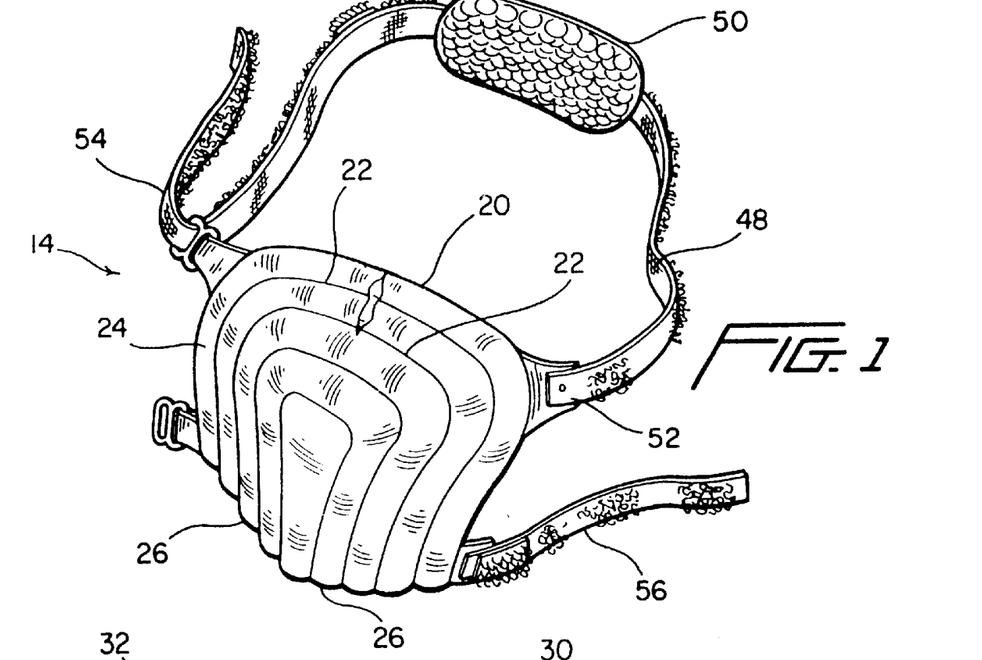
FIG. 1 shows a perspective view of a device for applying therapeutic thermal energy according to the present invention.
Figure 2:
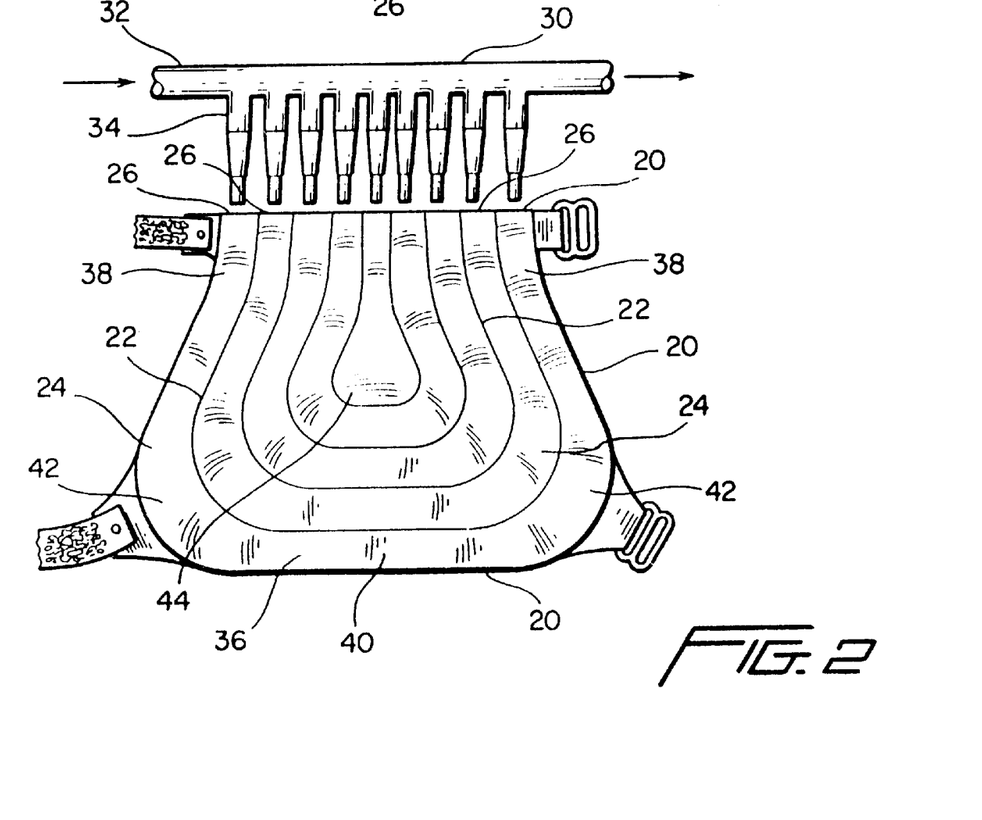
FIG. 2 shows a front view of the device shown in FIG. 1 being filled according to the present invention.
Figure 3:
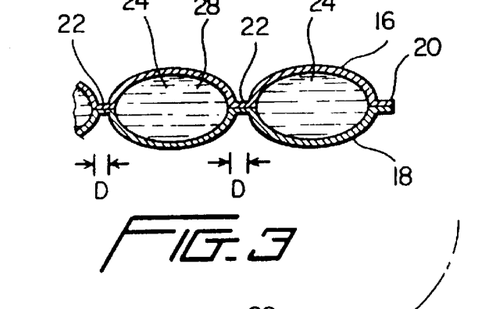
FIG. 3 shows a partial cross-sectional view of the device shown in FIG. 1 along the to line 3—3.

FIGS. 1–6 show a preferred embodiment of a device 14 for applying therapeutic thermal energy according to the present invention. Generally, a device 14 according to the present invention is formed from first and second layers, 16 and 18, respectively, of a deformable and resilient material, such as polyethylene sheet/strip material, which are sealingly connected along a common perimeter 20, as shown in FIGS. 1 and 3. Preferably, the sealing connection is formed from heat welding.

A device 14 according to the present invention is further characterized in that first layer 16 and second layer 18 are further sealingly connected along a plurality of, preferably congruent, curvilinear paths 22 within said perimeter 20. The sealing connection of first layer 16 to second layer 18 along paths 22 is preferably achieved by the same method as is used along perimeter 20, heat welding. Paths 22 are configured to define channels 24 having a preferably elliptical cross-section, between first layer 16 and second layer 18, as shown FIGS. 1–6. However, paths 22 may be configured to provide other configurations to each channel 24. For example, channel 24 may be configured such that each channel within layer 16 defines a radius of curvature greater than that of layer 18. This feature is particularly desirous in the event two modes of heat transfer are desired. Specifically, the layer 16 of a channel having a greater radius of curvature will tend to contact the surface of a treatment site to a greater extent, and thus apply thermal energy to the site at a greater rate, than a layer 18 of a channel having a lesser radius of curvature.

Paths 22 are further configured to provide a distance, D, between adjacent channels 24. The distance, D, between adjacent channels allows for articulation between adjacent channels, an important feature of the present invention which will be discussed further. Distance, D, also serves to ensure that adjacent channels remain preferably independent from one another such that each channel is provided with an independent channel volume. Each channel 26 is preferably at least partially filled with a medium 28 having a viscosity, preferably, greater than that of water, as shown in FIG. 3.

As shown in FIGS. 1–6, each channel 24 is provided with ends 26. At least one end 26 of each channel 24 is defined by perimeter 20 of device 14 according to the present invention. It is further preferable for the ends 26 of channels 24 defined by perimeter 20 to be adjacent one another, as shown in FIGS. 1–6. It is even further preferred for ends 26 which are defined by perimeter 20 to be even with one another, in other words, to define a plane, as shown in FIGS. 1–6.

During the manufacture of a device 14 according to the present invention, it is preferred for a pre-selected section of perimeter 20 to be maintained in an open or non-sealingly connected configuration to allow for filling of the channels 24 with a medium 28 according to the present invention. Preferably, device 14 is formed such that the section of perimeter 20 in common with the ends 26 of channels 24 is left open thereby allowing each channel to be filled individually according to the present invention.

Each channel 26 of device 14 is shown being filled with a medium 28 according to the present invention in FIG. 2. Specifically, device 14 is held such that the open pre-selected section 30 of perimeter 20 is maintained in a vertical orientation relative to a manifold 32. Manifold 32 is provided with nozzles 34 configured for filling each channel 24 with a medium 28 according to the present invention. Note that nozzles 34 may be configured to provide different types of medium 28. For example, it may be desirable to fill some channels with a first medium having a first specific heat and a first viscosity characteristic and some channels with a second medium having a second specific heat and a second viscosity characteristic. After filling, pre-selected section 30 is sealingly connected, preferably by heat welding, to complete perimeter 20 and the construction of device 14.

Filling of device 14 is greatly facilitated if each channel 24 is characterized by a fill constant according to the present invention. Specifically, channels 24 are preferably constructed such that the independent channel volume for each channel divided by the total number of ends 26 of that channel in common with the pre-selected perimeter section 30 is constant. A fill constant allows for nozzles 34 to have the same flow rate and thus uniform filling of each channel 24 is accomplished simply by activating manifold 32 for a duration of time. It is important to note that this feature as well as the aforementioned features of a device according to the present invention allow for high speed, low cost manufacturing.

The perimeter 20 and paths 22 of a device 14 according to the present invention are preferably configured to allow the device to adapt easily to the surface contours of the anatomy where treatment is desired. Device 14 shown in FIGS. 1–6 is configured for application of thermal energy to the shoulder. Specifically, paths 22 of device 14 are configured to provide a plurality of channels 24, each having a base portion and a pair of extending portions which extend substantially in the same direction, as shown in FIG. 2. Preferably, each base portion 36 is further characterized by a straight portion 40 and a pair of opposed acute angles 42, as is further shown in FIG. 2. Device 14 further includes a pleat 46. Preferably, pleat 46 is formed by heat welding a pair of equivalent length sections of perimeter 20, as shown in FIG. 5. Pleat 46 allows device 14 to transition from the somewhat spherical contour of the shoulder to the more cylindrical contour of the collar bone region of the body. Device 14 also includes a center channel 44 having only a single end 26 defined by pre-selected perimeter portion 30.

Figure 4:
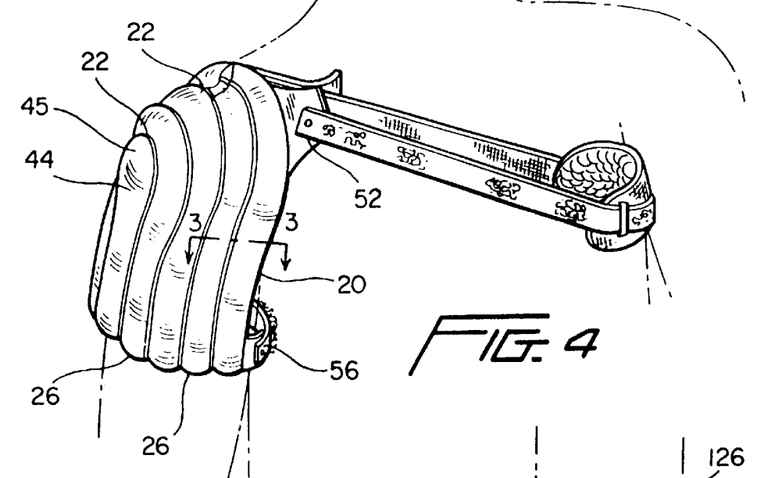
FIG. 4 shows a perspective view of the device shown in FIG. 1 in use on the shoulder of a human according to the present invention.
Figure 5:
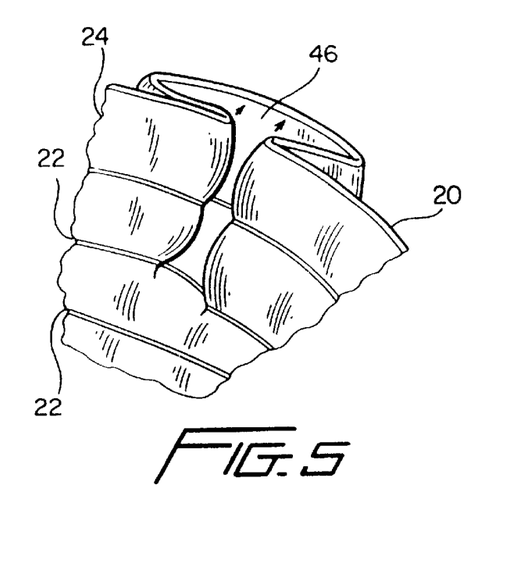
FIG. 5 a partial perspective view of the device shown in FIG. 1.
Figure 6:
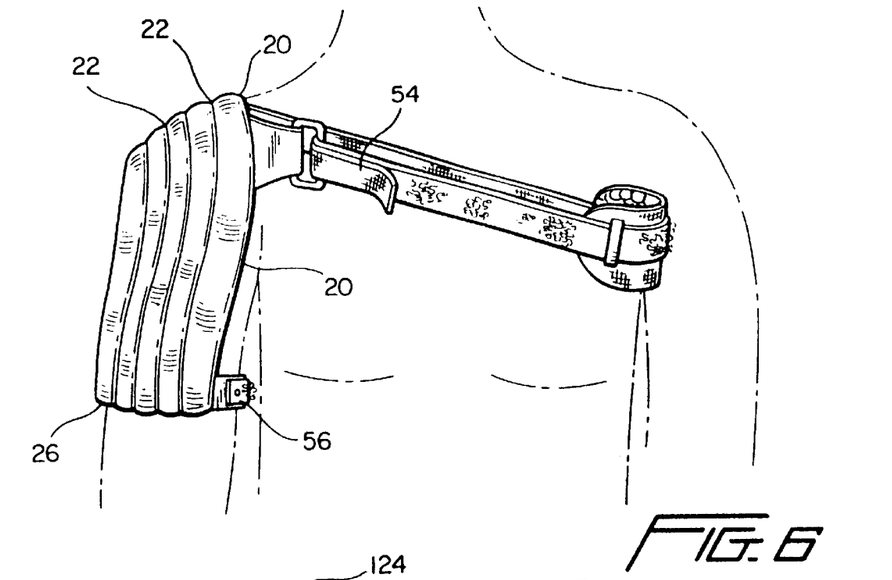
FIG. 6 shows a front view of the device in use shown in FIG. 4.

Device 14 is shown in use on the shoulder of an individual in FIGS. 4 and 6. It is important to note the manner in which paths 22 allow each channel 24 to adjust according to the topography of the shoulder. Moreover, paths 22 cause the medium within each channel 24 to be maintained uniformly throughout device 14, and thus, a uniform application of thermal energy to the treatment site. The base portion 45 of center channel 44 is somewhat enlarged to provide device 14 with the surface area and thermal capacity necessary to adequately apply thermal energy to the deltoid region of the shoulder.

Device 14 is shown secured to the body by a pair of straps. Specifically, a first strap 48 includes a first end 52 connected to an upper rear portion of device 14, a pad 50 movably secured thereto, and a second end 54 releasably connectable, preferably by hook and loop material, to an upper front portion of device 14, as shown in FIGS. 1, 4 and 6. A second strap 56 is configured similarly for securing the device to the arm of the wearer. It is important to note that the second end 54 of first strap 48 may always be maintained oriented to the front of the wearer and, thus, easily accessed, because device 14 is reversible. In other words, either layer 16 or 18 may be placed against the treatment site.

Figures 7, 8, 9:
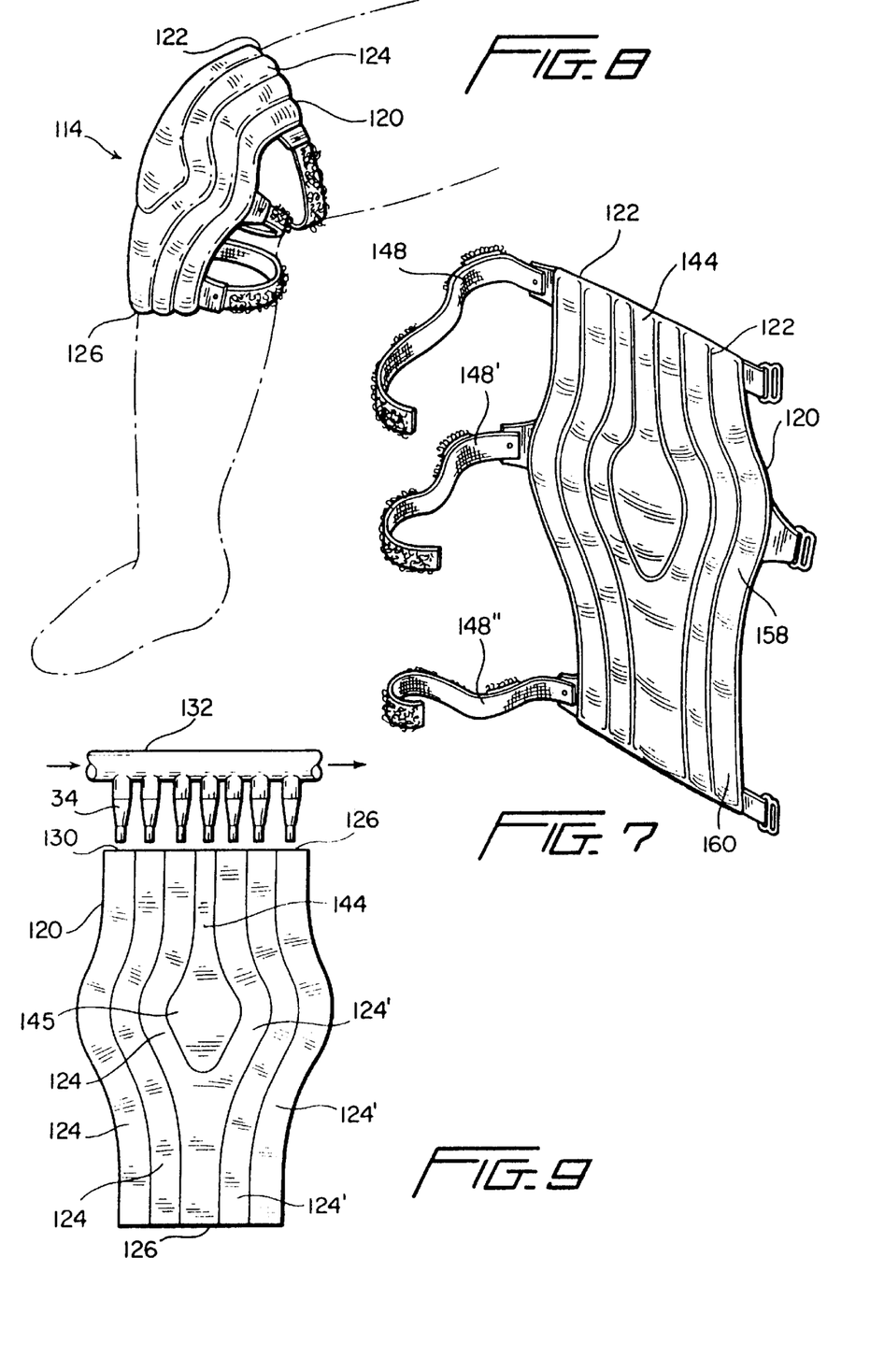
FIG. 7 shows a perspective view of another device for applying therapeutic thermal energy according to the present invention.
FIG. 8 shows a perspective view of the device shown in FIG. 7 in use on the knee of a human according to the present invention.
FIG. 9 shows a front view of the device shown in FIG. 7 being filled according to the present invention.
Figure 10:
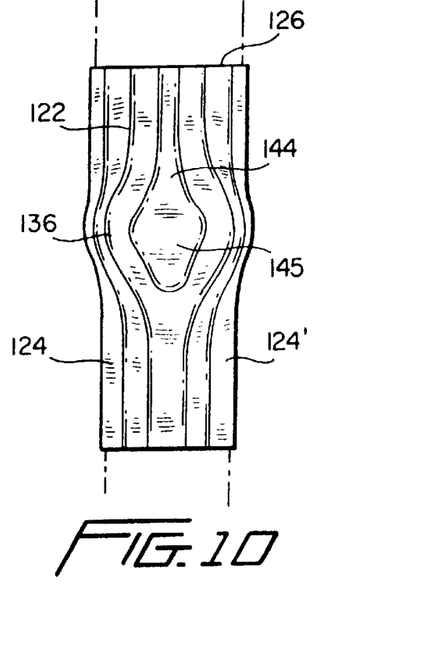
FIG. 10 shows a front view of the device shown in FIG. 7.
Figure 11:
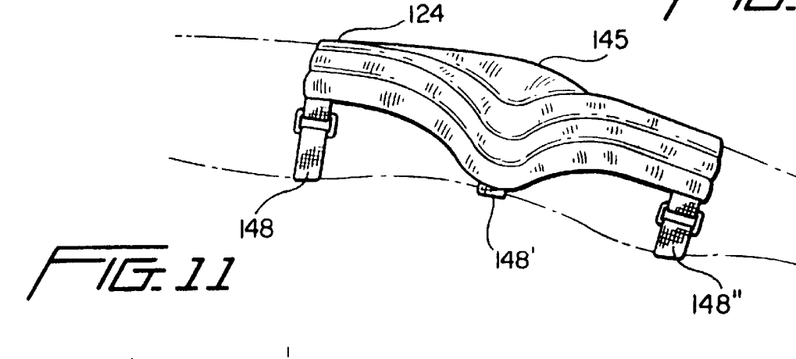
FIG. 11 shows a side view. of the device shown in FIG. 7.
Figure 12:
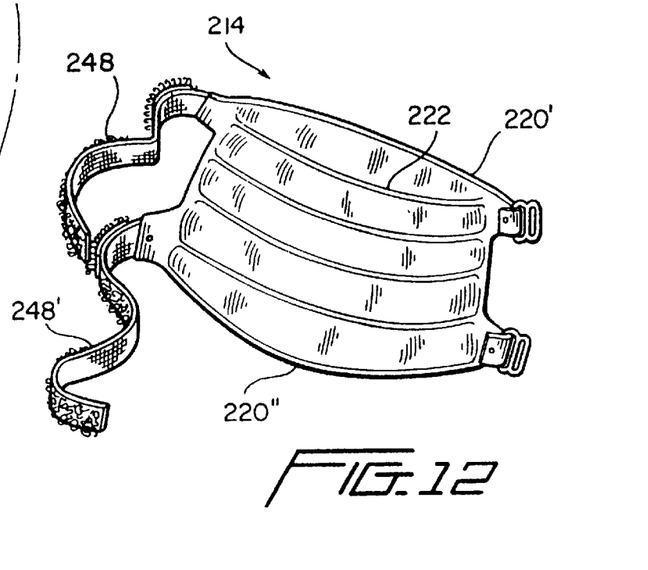
FIG. 12 shows a perspective view of another device for applying therapeutic thermal energy according to the present invention.

FIGS. 7–11 show a device 114 according to the present invention for applying therapeutic thermal energy to the knee. Paths 122 are configured to provide first and second sets of substantially congruent channels 124 and 124', respectively. Each channel includes a base portion 136 having a radius of curvature 158 and a pair of extending portions 160 which extend substantially in opposite directions. First set of channels 124 and second set of channels 124' are preferably symmetrical about a longitudinal centerline of device 114 as shown in FIG. 9. Device 114 preferably includes a center channel 144 which is provided with an enlarged base portion 145 for accommodating the patella region of the knee as shown in FIGS. 10 and 11. Center channel 144 also provides device with a larger upper portion for accommodating the typically larger circumference of the thigh, whereas the smaller lower portion of the device easily accommodates the shin or calf of the leg, as shown in FIG. 10.

FIG. 9 shows device 114 being filled according to the present invention. Specifically, the pre-selected section 130 of device 114 is shown oriented to nozzles 134 of manifold 132. Note that a single manifold and nozzle apparatus may be used to fill any number of devices according to the present invention.

Device 114 is shown being worn on the knee in FIGS. 10 and 11. Note that device 114 includes a first strap 148 for securing the device to the leg above the knee, a second strap 148' configured for securing the device to the leg at the knee and the a third strap configured for securing the device to the leg below the knee.

FIGS. 12–16 show a device 214 according to the present invention for applying therapeutic thermal energy to the ankle. Paths 222 are configured to provide a set of substantially congruent channels 224 each having a substantially identical radius of curvature. Device 214 is provided with an upper perimeter portion 220' and a lower perimeter portion 220". Each channel 224 is configured to become successively longer from upper perimeter portion 220' to lower perimeter portion 220".

Figure 14:
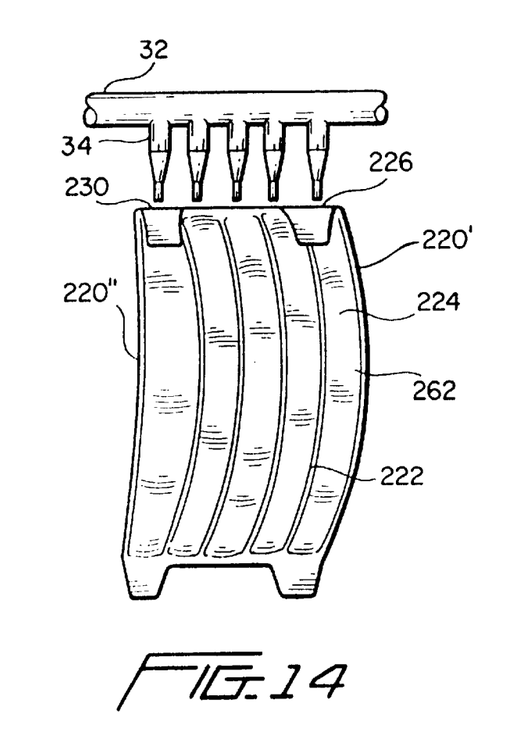
FIG. 14 shows a front view of the device shown in FIG. 12 being filled according to the present invention.

FIG. 14 shows device 214 being filled according to the present invention. Note that a pair of straps 248 and 248' are preferably attached to the perimeter 220 of device 214 after device 214 is filled.

Figure 13:
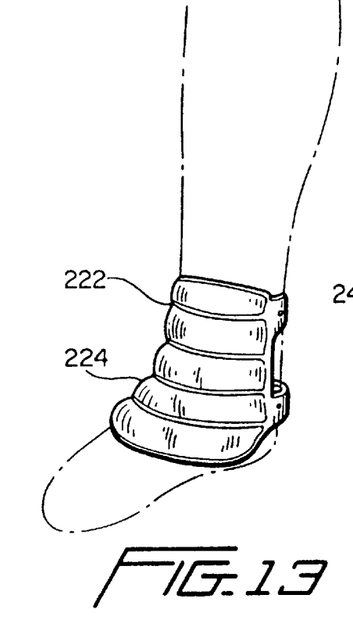
FIG. 13 shows a perspective view of the device shown in FIG. 12 in use on the ankle of a human.
Figure 15:
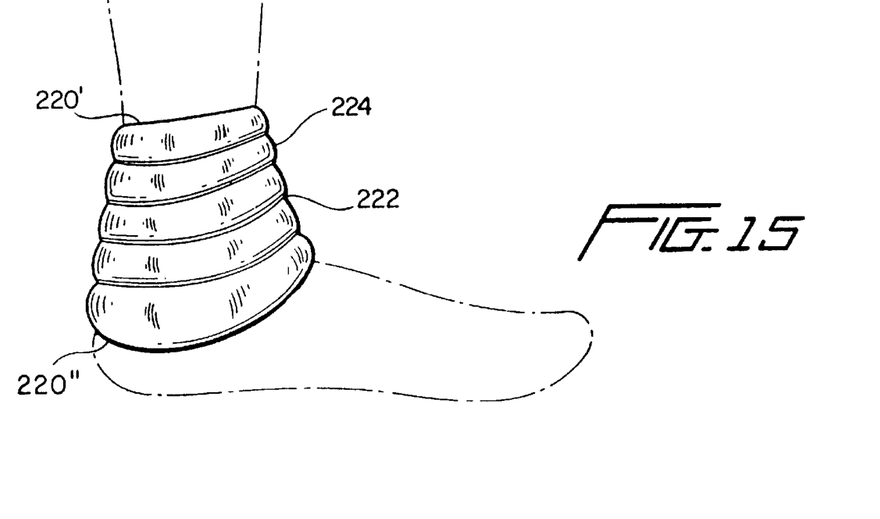
FIG. 15 shows a front view of the device shown in FIG. 12 being used at another position relative to the ankle.
Figure 16:
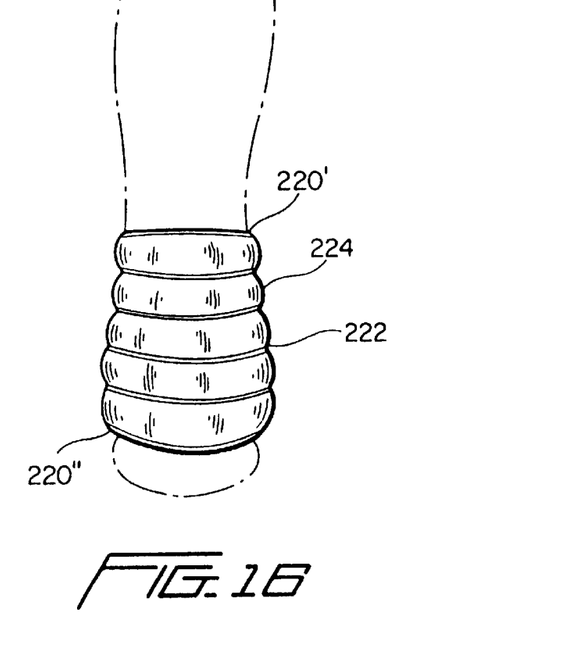
FIG. 16 shows front view of the device shown in FIG. 12 being used at another position relative to the ankle.

A typical use of device 214 is shown in FIG. 13. Specifically, device 214 is secured such that the surface area of the top surface of the foot and front surface of the shin are contacted by the device as shown in FIG. 13. It is important to note however that the configuration of device 214 provides versatility to the manner in which device 214 is secured to the ankle. Specifically, the configuration of device 214 allows device to be secured to the side of an ankle, as shown in FIG. 15 or to the Achilles tendon region of the ankle, as shown in FIG. 16.

Figure 17:
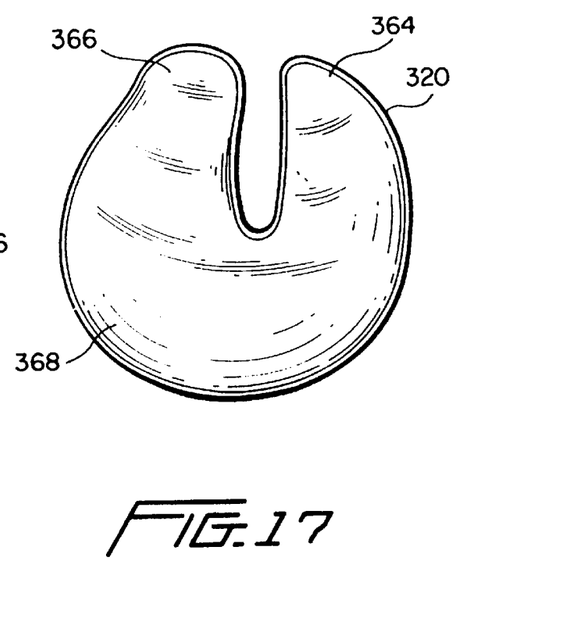
FIG. 17 shows a front view of another device for applying therapeutic thermal energy according to the present invention.
Figure 18:
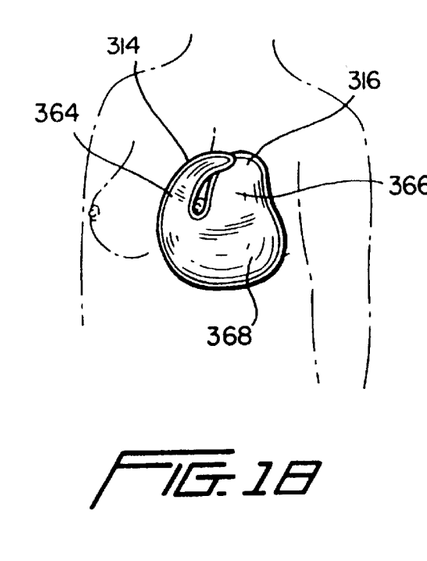
FIG. 18 shows a perspective view of the device shown in FIG. 17 in use on the left breast.
Figure 19:
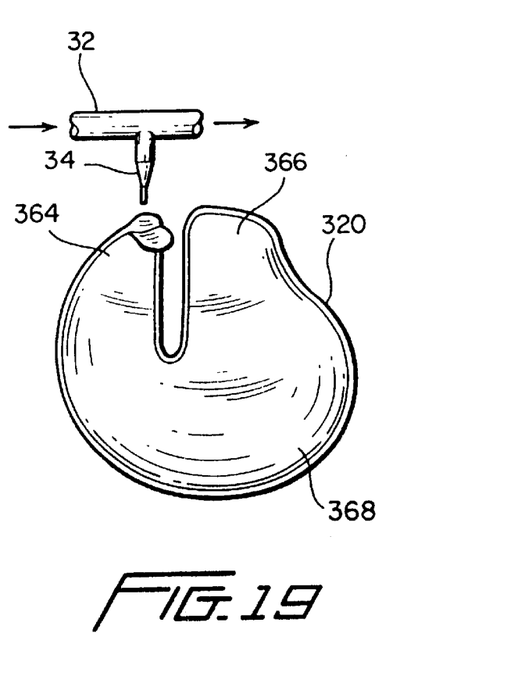
FIG. 19 shows front view of the device shown in FIG. 17 being filled according to the present invention.
Figure 20:
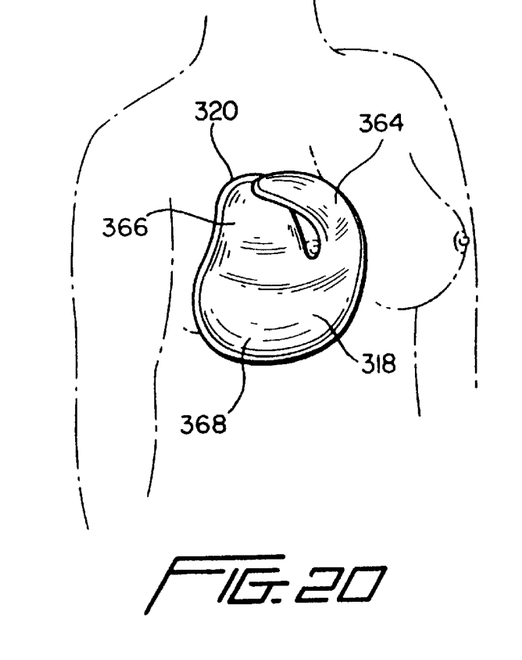
FIG. 20 shows a perspective view of the device shown in FIG. 17 in use on the right breast.

FIGS. 18–20 show a device 314 for applying thermal energy to the breast according to the present invention. Device 314 provides a preferably deformable and resilient first layer 316 sealingly connected to a deformable and resilient second layer 318 along a common perimeter 320. Layers 316 and 318 define a volume which is at least partially filled with a medium having a viscosity according to the present invention as shown in FIG. 19. Layers 316 and 318 further define a first half circle shape section 364 and a second half circle shaped section 366 as shown in FIGS. 17–20.

Device 314 is shown being worn according to the present invention in FIGS. 18 and 20. Device 314 includes a bifurcation 370 which preferably originates from a center of the device and extends substantially upwardly between first section 364 and second section 366, as shown in FIG. 17. Bifurcation 370 allows a nipple of the human breast to remain substantially free of contact with device 314. Moreover, bifurcation 370 allows first section 364 to partially overlap second section 366 as shown in FIGS. 18 and 20 to produce a conical and, thus, substantially breast congruent, configuration.

It is important to note that second section 366 of device 314 is provided with an extending section 368 which extends substantially downwardly and sideways, as shown in FIGS. 18 and 20. This section is particularly useful for treating a region of the breast which is somewhat remote from the main portion of the breast and moreover, extending region 368 provides a device 314 which uniformly stands off a bra or other undergarment from the surface of the breast.

What is claimed is:

1. A device for applying thermal energy to a human or animal, comprising:
    a deformable and resilient first layer sealingly connected to a deformable and resilient second layer along a common perimeter;
    said first layer further sealingly connected to said second layer along a plurality of curvilinear paths within said perimeter,
    said paths defining a plurality of channels between said first layer and said second layer,
    said paths being configured to allow articulation between adjacent channels,
    each said channel having at least one end defined by said common perimeter,
    said at least one end of each said channel being directly adjacent said at least one end of another said channel;
    each said channel being at least partially filled with a medium;
    wherein said device is configured for application of thermal energy to the human shoulder and said paths are configured to provide a plurality of channels each having a base portion and a pair of extending portions which extend substantially in the same direction; and
    wherein each said base portion includes a substantially straight section and a pair of opposed identical acute angles.

2. A device according to claim 1, wherein said paths are configured such that each said channel is sealed relative to each other said channel thereby providing each said channel with an independent channel volume.

3. A device according to claim 2, wherein each said channel is characterized by a fill constant defined by said independent channel volume divided by a total number of ends of said channel in contact with a defined side of said common perimeter.

4. A device according to claim 1, wherein said ends of said channels define a single plane.

5. A device according to claim 1, wherein each said channel defines an elliptical cross-section.

6. A device according to claim 1, wherein at least two of said paths are congruent.

7. A device according to claim 1, wherein at least two of said paths are topographically descriptive of an anatomical site.

8. A device according to claim 1, wherein said first layer and said second layer are made of polyethylene and said first layer and said second layer are sealingly connected by heat welding.

9. A device according to claim 1, wherein said medium varies among at least two said channels.

10. A device according to claim 1, wherein said viscosity of said medium varies among at least two said channels.

11. A device according to claim 1, wherein one of said base portions of a channel adjacent said perimeter is provided with at least one pleat.

12. A device according to claim 11, wherein said device includes a center channel.

13. A device according to claim 12, wherein said device includes a first strap configured for securing the device to the torso of the body.

14. A device according to claim 13, wherein said first strap includes a first end connected to an upper rear portion of said device, a pad movably secured to the strap for interposing between said strap and said rib cage of said torso, and a second end releasably connectable to an upper front portion of said device.

15. A device according to claim 14, wherein said device includes a second strap configured for securing the device to an arm of the body.

16. A device according to claim 15, wherein said second strap includes a first end connected to a lower rear portion of said device and a second end releasably connectable to a lower front portion of said device.

* * * * *